US011925384B1

(12) United States Patent
Hacker (10) Patent No.: US 11,925,384 B1
(45) Date of Patent: Mar. 12, 2024

(54) LIGHT TRANSMISSIBLE END CAP WITH LENS AND BAYONET

(71) Applicant: Nano Surgical, LLC, Delray Beach, FL (US)

(72) Inventor: Steven M. Hacker, Delray Beach, FL (US)

(*) Notice: Subject to any disclaimer, the term of this patent is extended or adjusted under 35 U.S.C. 154(b) by 111 days.

(21) Appl. No.: 17/856,110

(22) Filed: Jul. 1, 2022

(51) Int. Cl.
*A61B 17/3211* (2006.01)
*F21V 5/04* (2006.01)
*F21V 21/40* (2006.01)
*F21V 33/00* (2006.01)

(52) U.S. Cl.
CPC .......... *A61B 17/3211* (2013.01); *F21V 5/048* (2013.01); *F21V 21/40* (2013.01); *F21V 33/0068* (2013.01); *F21V 2200/00* (2015.01)

(58) Field of Classification Search
CPC .... A61B 2018/2266; A61B 2018/1807; A61B 2018/2255; F21V 5/048; F21V 33/0068; F21V 21/40
See application file for complete search history.

(56) References Cited

U.S. PATENT DOCUMENTS

| 2014/0303449 | A1* | 10/2014 | Balog | A61B 18/1402 600/249 |
| 2018/0318034 | A1* | 11/2018 | Julian Ibañez | A61B 90/361 |
| 2020/0038049 | A1* | 2/2020 | Hacker | A61B 17/32002 |
| 2020/0121305 | A1* | 4/2020 | Komsa | A61B 18/1402 |

* cited by examiner

*Primary Examiner* — Julie A Bannan
(74) *Attorney, Agent, or Firm* — Nancy J. Flint, Attorney At Law, P.A.; Nancy J. Flint (57) ABSTRACT

A light transmissible end cap comprising a lens and bayonet that can be attached to a handle is disclosed. The lens and the bayonet are light transmissible. The end cap can be attached to a handle of any shape, reversibly or non-reversibly, to create a light transmissible scalpel handle that can transmit, amplify, diverge and/or converge light from a light source disposed within the handle through the end cap, the lens and the bayonet. A universal blade fitting may be attached to the bayonet. The handle may be a surgical handle.

20 Claims, 10 Drawing Sheets

LIGHT TRANSMISSIBLE END CAP WITH LENS AND BAYONET

FIELD OF THE INVENTION

The invention relates to the field of mechanical cutting instruments. In particular, the invention relates to a light transmissible end cap comprising a lens and bayonet that can be attached to a handle. The lens and the bayonet may comprise various materials and shapes that are light transmissible. The end cap can be attached to a handle of any shape, reversibly or non-reversibly, to create a light transmissible scalpel handle that can transmit, amplify, diverge and/or converge light from a light source disposed within the handle through the end cap, the lens and the bayonet. A universal blade fitting may be attached to the bayonet. In one embodiment, the handle is a surgical handle.

BACKGROUND OF THE INVENTION

Physicians and surgeons use a handle attached to a blade to cut human tissue for a variety of purposes. The handle is typically one-piece and may have various shapes. At the end furthest from the handle grip typically there is an opaque end with an opaque stainless-steel bayonet.

Many shapes and materials are known to be used for handles, ranging from round to flat in shape and plastic, stainless-steel and aluminum in material and some with an illumination source.

U.S. Pat. No. 8,690,872 titled SURGICAL PENCIL ENABLING SUCTION discloses surgical pencils defining a channel to enable suctioning of materials.

U.S. Pat. No. 7,172,611 titled SURGICAL SCALPEL ASSEMBLY discloses a surgical scalpel assembly includes a handle having at least one attachment element and at least one guide element.

U.S. Pat. No. 9,181,352 titled SCALPEL WITH REMOVABLE BLADE ASSEMBLY discloses a surgical blade device similar to a disposable scalpel wherein the blade assembly is easily replaceable.

U.S. Pat. No. 8,291,601 titled REUSABLE METAL BLADE HANDLE discloses a reusable metal blade scalpel handle with safety features provided therein which are also usable across a wide range of blades.

U.S. Design Pat. No. D704337 titled SCALPEL HANDLE discloses a scalpel handle designed to receive a scalpel blade and be used by medical personnel during surgical procedures.

U.S. Pat. No. 8,409,231 titled SCALPEL HANDLE discloses a contoured scalpel handle that provides for increased contact area with the user's hand using a larger diameter central portion and a smaller diameter trough.

U.S. Pat. No. 8,409,232 titled SURGICAL INSTRUMENT ASSEMBLY discloses a surgical instrument assembly configurable for performing a dermatotomy in a percutaneous procedure and further configurable for performing cuts in open surgery includes a pointed scalpel blade and a hollow sheath body disposed to encapsulate the pointed scalpel blade inside a longitudinal instrument cavity to protect a user.

U.S. patent Ser. No. 10/610,257 titled STRUCTURAL ELEMENT WITH BAYONET HAVING A UNIVERSAL BLADE FITTING WITH ELECTRICAL SOURCE POD AND TERMINAL CONFIGURATION discloses an assembly having a support element with a bayonet having a universal blade fitting inserted into the interior of a tube and an electrical source pod.

U.S. Pat. No. 9,072,541 titled SURGICAL SCALPEL HANDLE WITH ILLUMINATOR discloses a surgical scalpel handle with illuminator allowing the surgeon to use the illumination to light the surgical field while holding the scalpel handle.

BRIEF SUMMARY OF THE INVENTION

One embodiment of the invention relates to a light transmissible end cap comprising a lens and bayonet that can be attached to a handle. The lens and the bayonet may comprise various materials and shapes that are light transmissible. The end cap can be attached to a handle of any shape, reversibly or non-reversibly, to create a light transmissible scalpel handle that can transmit, amplify, diverge and/or converge light from a light source disposed within the handle through the end cap, the lens and the bayonet. A universal blade fitting may be attached to the bayonet. In one embodiment, the universal blade fitting comprises stainless-steel and the handle is a surgical handle. In one embodiment of the invention, a blade backstop is disposed on the bayonet such that a blade attached to the universal blade fitting abuts the blade backstop.

In one embodiment of the invention, the light transmissible end cap comprising a lens and bayonet is made of a material that can be reused.

In one embodiment of the invention, the light transmissible end cap comprising a lens and bayonet is made of a material that can be discarded after use.

In one embodiment of the invention, the universal blade fitting comprises opaque material.

In one embodiment of the invention, the universal blade fitting comprises transparent material.

In one embodiment of the invention, the light transmissible end cap with lens and bayonet can be inserted into a handle of different shapes and sizes to enable the handle to be used without breaking off the universal bayonet fitting and blade during surgery.

In one embodiment of the invention, the light transmissible end cap with lens and bayonet can reversibly or non-reversibly be inserted into a handle of different shapes and sizes in a manner that prevents contamination to the hollow of the handle.

In one embodiment of the invention, the light transmissible end cap with lens and bayonet can reversibly or non-reversibly be inserted into a handle of different shapes and sizes in a manner that fits the ergonomic preference of a user, for example a surgeon.

In one embodiment of the invention, the lens is substantially flat. In one embodiment of the invention, the lens is convex. In one embodiment, the lens is concave.

BRIEF DESCRIPTION OF THE DRAWINGS

The various features of the invention and the manner of attaining them will be described in greater detail with reference to the following description, claims, drawings, wherein like designations denote like elements.

DETAILED DESCRIPTION OF THE INVENTION

The invention relates to a light transmissible end cap comprising a lens and a bayonet. The light transmissible end cap is separate from a light source disposed within a handle. The bayonet is also light transmitting and further comprises a universal blade fitting, which universal blade fitting may comprise stainless-steel. The light transmissible end cap can be attached to and used with any shape of handle. A light source is disposed within the handle such that light is transmitted through the end cap, through the lens and through the bayonet.

In one embodiment of the invention, the light source comprises the lens. The light transmissible end cap is attached to a handle and the bayonet comprises a universal blade fitting. In one embodiment of the invention, light is emitted from the light source through a tip that passes through the light transmissible end cap and bayonet. In one embodiment of the invention, the tip of the light source comprises a substantially flat lens, a concave lens or a convex lens.

According to one embodiment of the invention, the end cap is releasably attached to a handle. According to one embodiment of the invention, the end cap is permanently attached to a handle. According to one embodiment of the invention, the end cap is attached to the handle in a manner that prevents contamination of the interior of the handle.

According to one embodiment of the invention, the lens is substantially flat such that light from the light source within the handle is transmitted in substantially a straight line. According to one embodiment of the invention, the lens is substantially convex such that light from the light source within the handle is transmitted converges. According to one embodiment of the invention, the lens is substantially concave such that light from the light source within the handle is transmitted diverges.

According to one embodiment of the invention, a photographic or video recording device is disposed within the handle.

According to one embodiment of the invention, the universal blade fitting comprises any material. In one embodiment of the invention, the universal blade fitting comprises stainless steel. In one embodiment of the invention, the universal blade fitting comprises plastic. In one embodiment of the invention, the universal blade fitting is molded into the bayonet.

According to one embodiment of the invention, the universal blade fitting is designed in a manner to permit light that passes through and around the bayonet to diffuse from all sides of the bayonet.

According to one embodiment of the invention, the universal blade fitting can be designed to attach to any type of blade as desired by the user. According to one embodiment of the invention, the blade is inserted onto the universal blade fitting and abuts the blade backstop.

According to one embodiment of the invention, the end cap, lens and bayonet comprise disposable material of construction that is disposed of following surgery. According to one embodiment of the invention, the end cap, lens and bayonet comprise reusable material of construction that can be sterilized following surgery for reuse.

According to one embodiment of the invention, the lens comprises any light transmissible material including optical glass, crystals and plastics and mirrors, in combination or alone, and may be a reusable material of construction that can be sterilized following surgery for reuse.

Figure 1A:
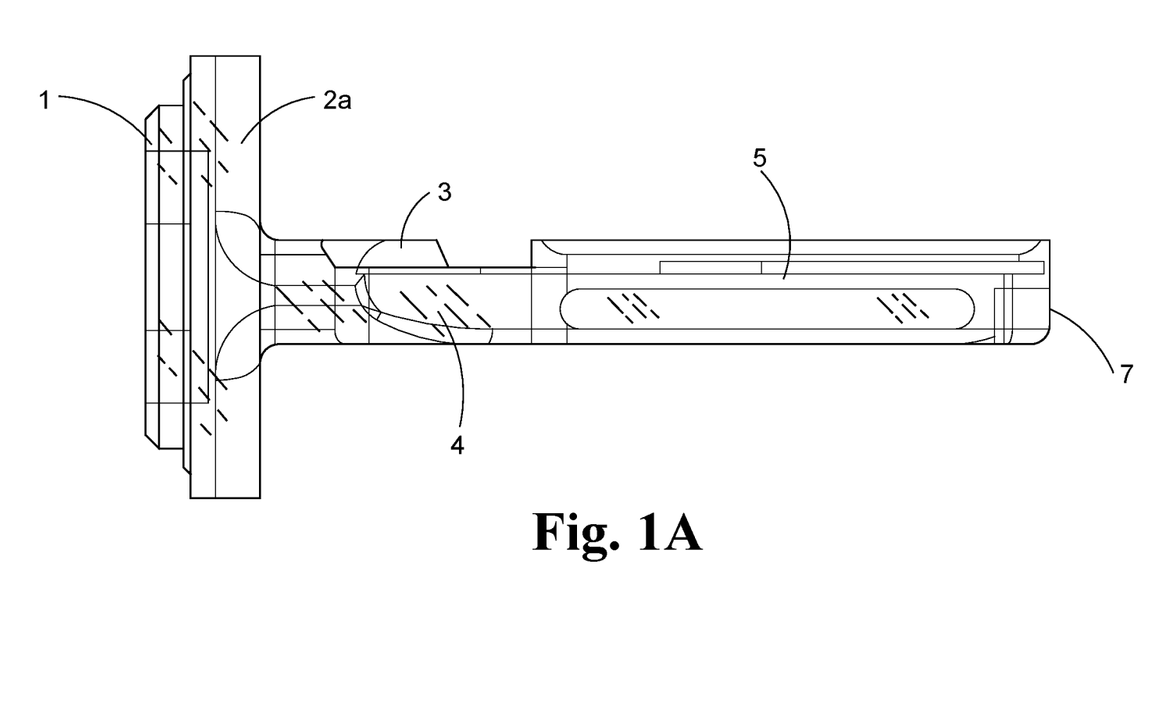
FIG. 1A is a top view of a light transmissible end cap comprising a flat lens and bayonet having a stainless-steel universal blade fitting according to one embodiment of the invention.

Turning to the figures, FIG. 1A depicts a top view of a light transmissible end cap 1 having a substantially flat lens $2a$ and bayonet 4 having a blade backstop 3 a universal blade fitting 5 and a bayonet tip 7, according to one embodiment of the invention. Bayonet 4 is light transmissible. Universal blade fitting 5 comprises stainless-steel according to one embodiment of the invention. Light transmissible end cap 1 is attached to a handle (not shown) in which is disposed a light source (not shown).

Figure 1B:
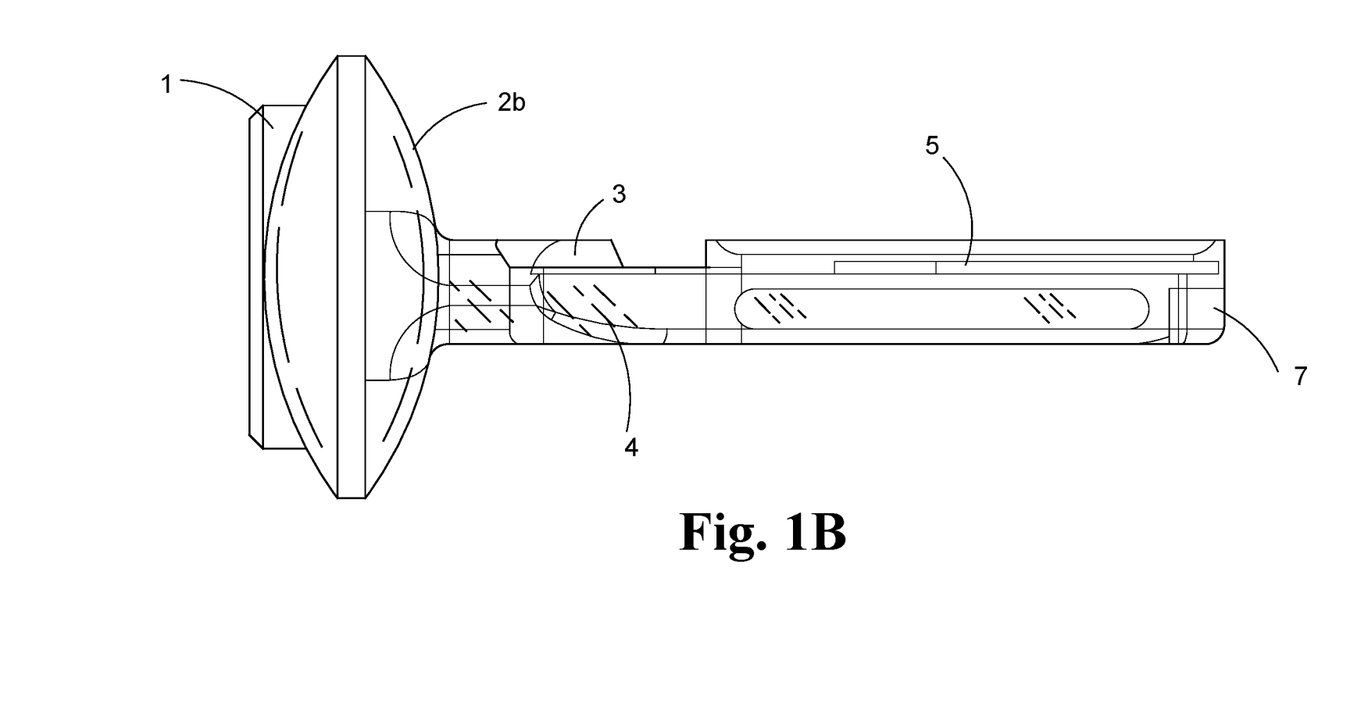
FIG. 1B is a top view of a light transmissible end cap comprising a convex lens and bayonet having a stainless-steel universal blade fitting according to one embodiment of the invention.

FIG. 1B depicts a top view of a light transmissible end cap 1 having a convex lens $2_b$ and bayonet 4 having a blade backstop 3 a universal blade fitting 5 and a bayonet tip 7, according to one embodiment of the invention. Bayonet 4 is light transmissible. Universal blade fitting 5 comprises stainless-steel according to one embodiment of the invention.

Figure 1C:
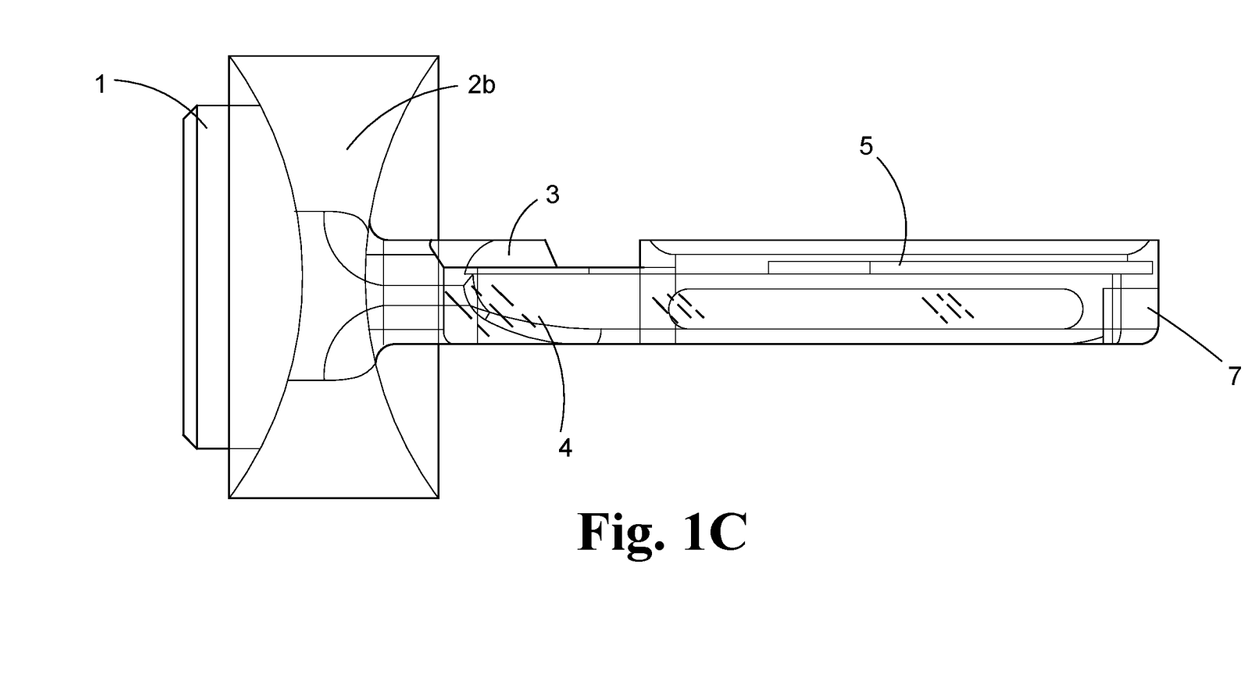
FIG. 1C is a top view of a light transmissible end cap comprising a concave lens and bayonet having a stainless-steel universal blade fitting according to one embodiment of the invention.

FIG. 1C depicts a top view of a light transmissible end cap 1 having a concave lens $2_c$ and bayonet 4 having a blade backstop 3 a universal blade fitting 5 and a bayonet tip 7, according to one embodiment of the invention. Bayonet 4 is light transmissible. Universal blade fitting 5 comprises stainless-steel according to one embodiment of the invention. Light transmissible end cap 1 is attached to a handle (not shown) in which is disposed a light source (not shown).

Figure 2A:
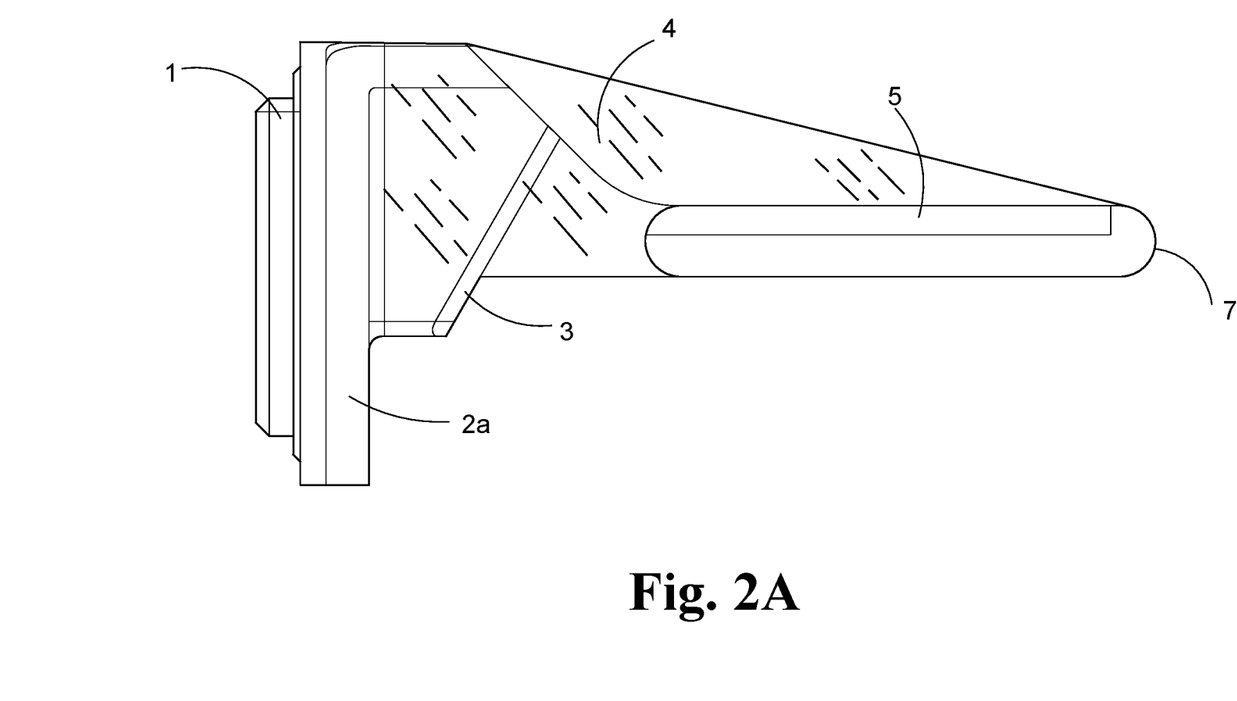
FIG. 2A is a side view of a light transmissible end cap comprising a flat lens and bayonet having a stainless-steel universal blade fitting according to one embodiment of the invention.

FIG. 2A is a side view of a light transmissible end cap 1 comprising a flat lens $2_a$ and bayonet 4 having a blade backstop 3 a universal blade fitting 5 and a bayonet tip 7 according to one embodiment of the invention.

Figure 2B:
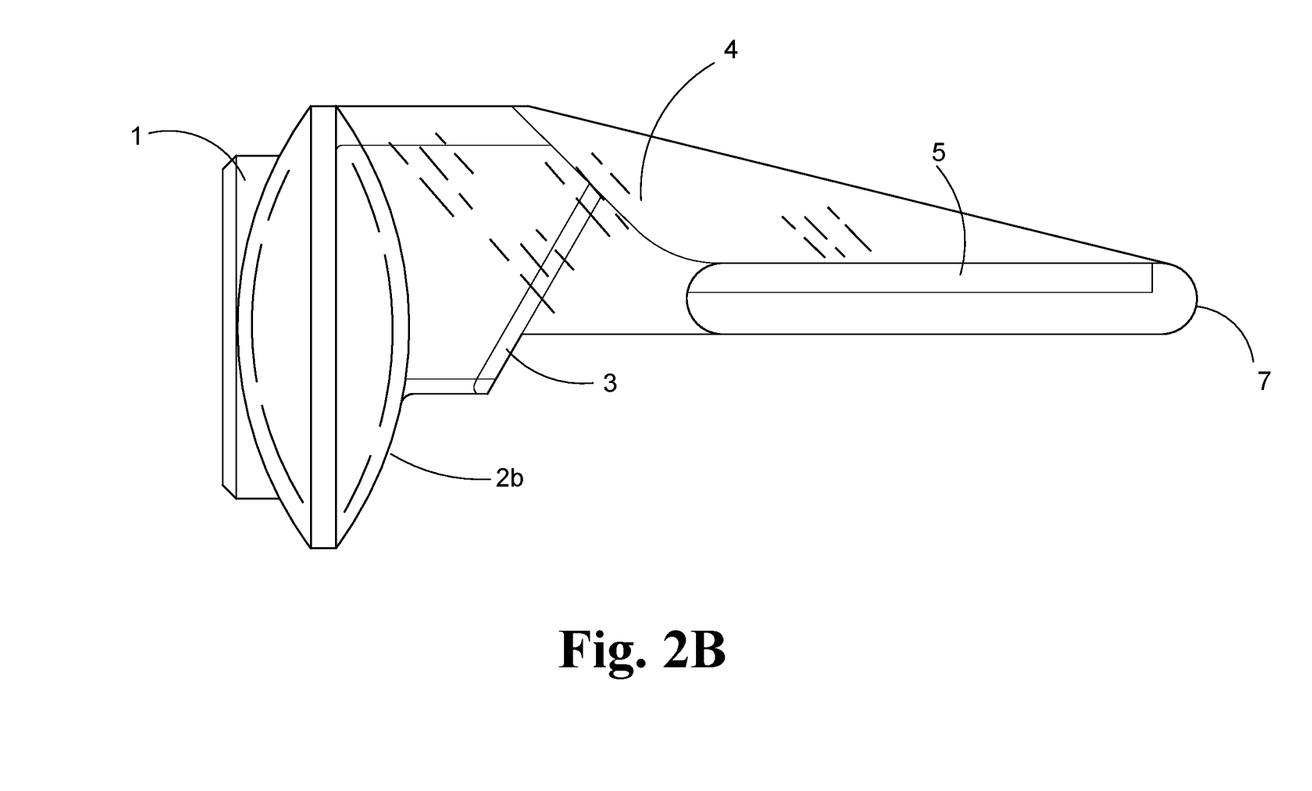
FIG. 2B is a side view of a light transmissible end cap comprising a convex lens and bayonet having a stainless-steel universal blade fitting according to one embodiment of the invention.

FIG. 2B is a side view of a light transmissible end cap 1 comprising a convex lens $2_b$ and bayonet 4 having a blade backstop 3 a universal blade fitting 5 and a bayonet tip 7 according to one embodiment of the invention.

Figure 2C:
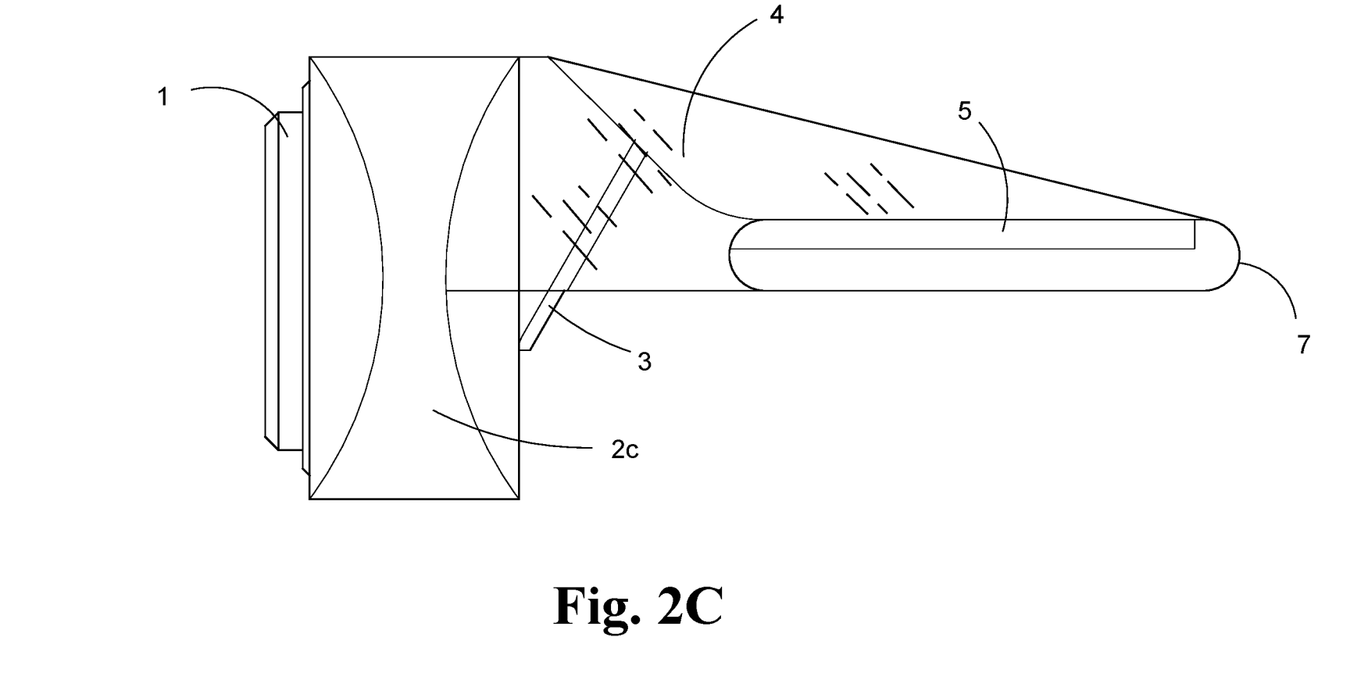
FIG. 2C is a side view of a light transmissible end cap comprising a concave lens and bayonet having a stainless-steel universal blade fitting according to one embodiment of the invention.

FIG. 2C is a side view of a light transmissible end cap 1 comprising a concave lens $2_c$ and bayonet 4 having a blade backstop 3 a universal blade fitting 5 and a bayonet tip 7 according to one embodiment of the invention.

Figure 3:
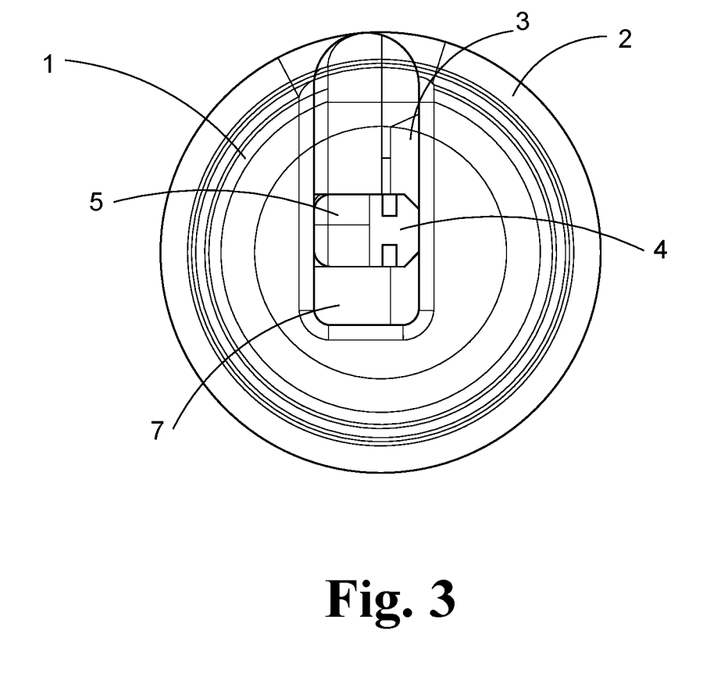
FIG. 3 is a front view of a light transmissible end cap comprising a lens and bayonet having a stainless-steel universal blade fitting according to one embodiment of the invention.

FIG. 3 depicts a front view of light transmissible end cap 1 having a substantially flat lens $2_a$ and bayonet 4 having a universal blade fitting 5. Light waves 6 are transmitted substantially directly through bayonet 4 to bayonet tip 7, although some light will diffract and transmit through all sides of bayonet 4.

Figure 4A:
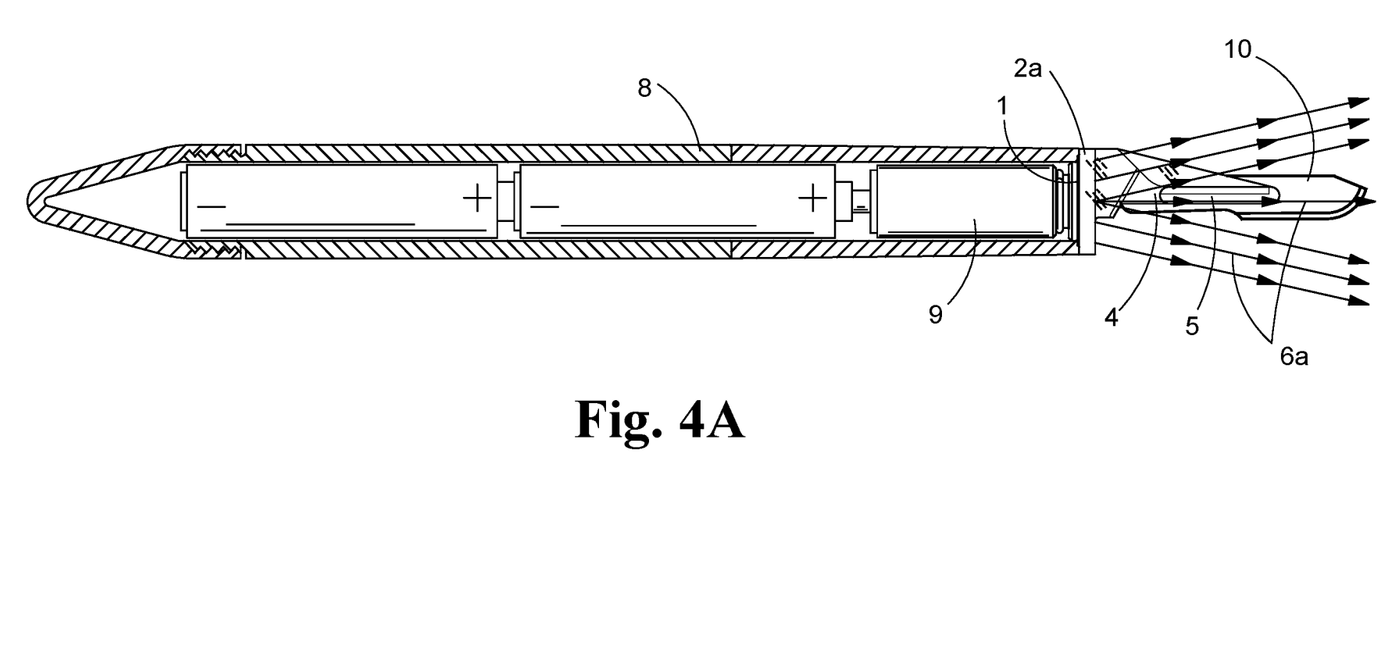
FIG. 4A is a top view of a light transmissible end cap comprising a flat lens and bayonet having a stainless-steel universal blade fitting attached to a handle according to one embodiment of the invention.

FIG. 4A is a cross-section view of a light transmissible end cap 1 comprising a flat lens $2_a$ and bayonet 4 having a stainless-steel universal blade fitting 5 attached to a handle 8 and having a blade 10 attached to universal blade fitting 5 according to one embodiment of the invention. A light source 9 is disposed in the interior of handle 8. Light 6 transmits from the light source 9 through end cap 1, through substantially flat lens $2_a$ and through bayonet 4. Light 6 transmits directly through universal blade fitting 5 and around blade 10. Some of transmitted light 6 will diffract and transmit through all sides of bayonet 4.

Figure 4B:
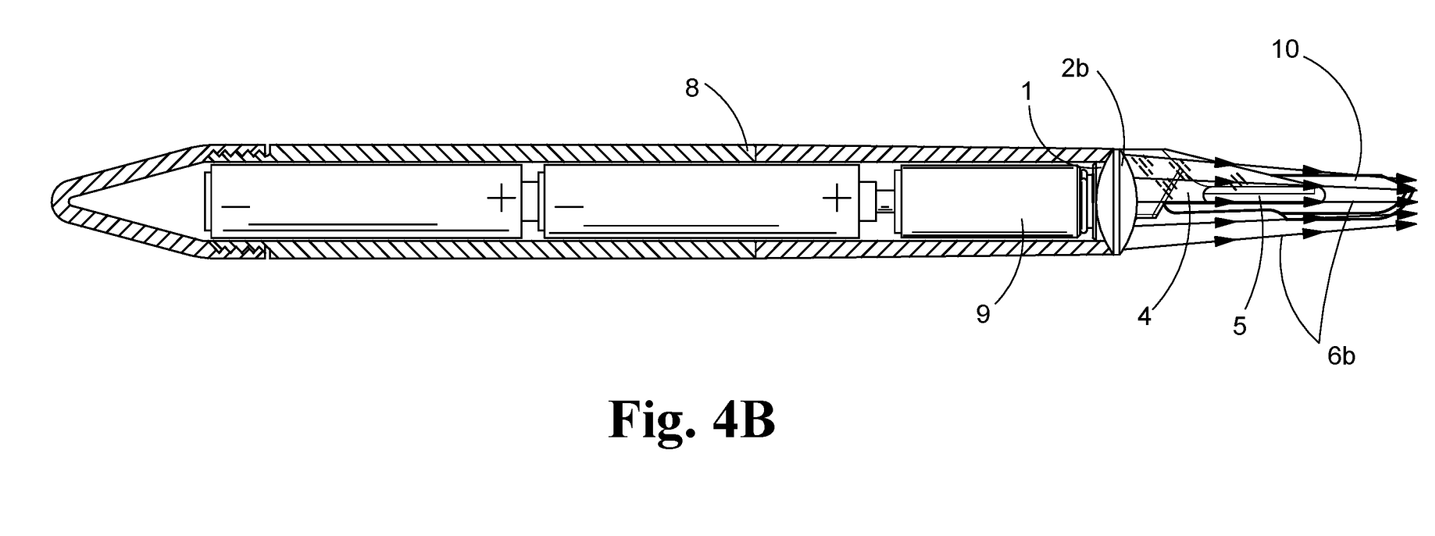
FIG. 4B is a top view of a light transmissible end cap comprising a convex lens and bayonet having a stainless-steel universal blade fitting attached to a handle according to one embodiment of the invention.

FIG. 4B is a cross-section view of a light transmissible end cap 1 comprising a convex lens $2_b$ and bayonet 4 having a stainless-steel universal blade fitting 5 attached to a handle 8 and having a blade 10 attached to universal blade fitting 5 according to one embodiment of the invention. A light source 9 is disposed in the interior of handle 8. Light 6 transmits in a convergent pattern through universal blade fitting 5 and around blade 10. Some of transmitted light 6 will diffract and transmit through all sides of bayonet 4.

Figure 4C:
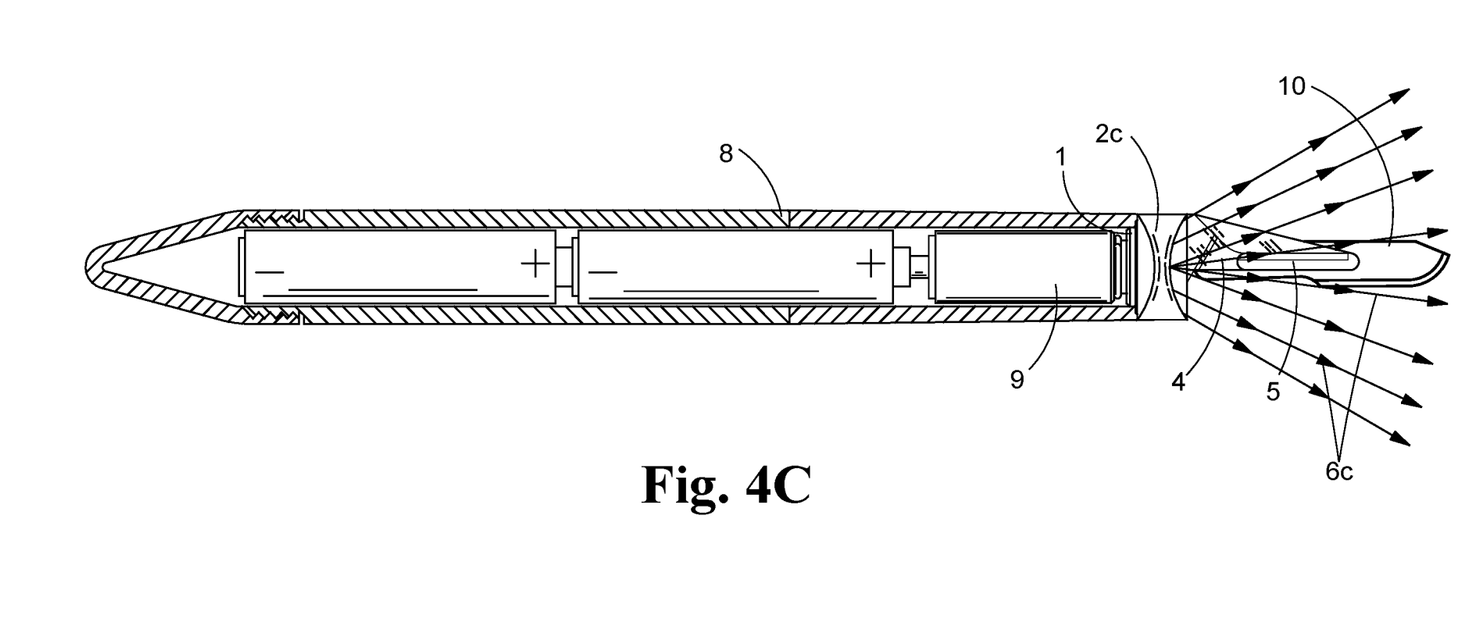
FIG. 4C is a top view of a light transmissible end cap comprising a concave lens and bayonet having a stainless-steel universal blade fitting attached to a handle according to one embodiment of the invention.

FIG. 4C is a cross-section view of a light transmissible end cap 1 comprising a concave lens $2_c$ and bayonet 4 having a stainless-steel universal blade fitting 5 attached to a handle 8 and having a blade 10 attached to universal blade fitting 5 according to one embodiment of the invention. A light source 9 is disposed in the interior of handle 8. Light 6 transmits in a divergent pattern through universal blade fitting 5 and around blade 10. Some of transmitted light 6 will diffract and transmit through all sides of bayonet 4.

While the invention has been described in reference to certain embodiments, it should be understood by those skilled in the art that various changes in form and detail may be made therein without departing from the scope and spirit of the invention encompassed by the claims. Although the embodiments have been described in reference to a an end cap lens that contains a lens and bayonet having a universal blade fitting that enables a handle, of any shape to attach to it, reversibly or non-reversibly, creating a light transmissible scalpel handle that can transmit, amplify, diverge or converge light from a light source, the invention may also apply to any instrument or device, or any medical device, that is used on or in the body for treating, excising, incising or diagnosing including but not limited to skin hooks, dental mirrors, retractors, elevators, probes, curettes, and other instruments and that contains an handle or a tubelike apparatus. Numerous modifications, changes, variations, substitution and equivalents will be apparent to those skilled in the art without departing from the spirit and scope of the invention as described in the claims.

What is claimed is:

1. A light transmissible end cap with bayonet and universal blade fitting comprising:
   an end cap, the end cap comprising a front face and a rear face;
   a bayonet attached to the front face of the end cap, the bayonet comprising a first end proximal the front face of the end cap and a distal end comprising a bayonet tip;
   a universal blade fitting attached to the bayonet; and
   a lens disposed within the space between the front face and rear face of the end cap,
   wherein the rear face of the end cap is designed to attach to a handle,
   wherein the universal blade fitting is designed to accommodate a blade,
   wherein the end cap, the lens and the bayonet are made of a light transmissible material.

2. The light transmissible end cap with bayonet and universal blade fitting of claim 1, further comprising a blade backstop disposed at the first end of the bayonet.

3. The light transmissible end cap with bayonet and universal blade fitting of claim 1, wherein the lens is substantially flat.

4. The light transmissible end cap with bayonet and universal blade fitting of claim 1, wherein the lens is convex.

5. The light transmissible end cap with bayonet and universal blade fitting of claim 1, wherein the lens is concave.

6. The light transmissible end cap with bayonet and universal blade fitting of claim 1, wherein the lens comprises optical glass, crystal, plastic or mirrors and combinations thereof.

7. The light transmissible end cap with bayonet and universal blade fitting of claim 1, wherein the universal blade fitting comprises an opaque material.

8. The light transmissible end cap with bayonet and universal blade fitting of claim 1, wherein the universal blade fitting comprises a transparent material.

9. The light transmissible end cap with bayonet and universal blade fitting of claim 1, wherein the universal blade fitting is of a unitary construction with the bayonet.

10. The light transmissible end cap with bayonet and universal blade fitting of claim 9, wherein the universal blade fitting is molded into the bayonet.

11. The light transmissible end cap with bayonet and universal blade fitting of claim 1, wherein the light transmissible end cap with bayonet and universal blade fitting is reusable.

12. The light transmissible end cap with bayonet and universal blade fitting of claim 1, wherein the light transmissible end cap with bayonet and universal blade fitting is disposable.

13. A handle attached to a light transmissible end cap with bayonet and universal blade fitting according to claim 1.

14. The handle attached to a light transmissible end cap with bayonet and universal blade fitting of claim 13, wherein the rear face of the end cap is reversibly attached to the handle.

15. The handle attached to a light transmissible end cap with bayonet and universal blade fitting of claim 13, wherein a light source is disposed within the interior of the handle, wherein the light is directed to pass through the light transmissible end cap and bayonet.

16. The handle attached to a light transmissible end cap with bayonet and universal blade fitting of claim 15, wherein a photographic or video recording device is disposed within the interior of the handle.

17. The handle attached to a light transmissible end cap with bayonet and universal blade fitting of claim 16, wherein the blade is a surgical blade.

18. The handle attached to a light transmissible end cap with bayonet and universal blade fitting of claim 13, wherein the lens comprises optical glass, crystal, plastic or mirrors and combinations thereof.

19. A scalpel handle comprising:

an end cap, the end cap comprising a front face and a rear face;

a bayonet attached to the front face of the end cap, the bayonet comprising a first end proximal the front face of the end cap and a distal end comprising a bayonet tip;

a universal blade fitting attached to the bayonet;

a handle attached to the rear face of the end cap, wherein the handle comprises a hollow interior; and a light source disposed in the interior of the handle, the light source comprising a tip through which light is emitted from the light source, wherein the light is emitted from the light source directionally through the end cap, wherein the universal blade fitting is designed to accommodate a blade, wherein the end cap and the bayonet are made of a light transmissible material, wherein the tip of the light source comprises a lens.

20. The scalpel handle of claim 19, wherein the lens comprises a substantially flat lens, a concave lens or a convex lens.

\* \* \* \* \*